(12) United States Patent
Fagerstam

(10) Patent No.: US 7,361,308 B2
(45) Date of Patent: Apr. 22, 2008

(54) SPOT PICKER DEVICE AND METHOD FOR PICKING GEL PLUGS

(75) Inventor: Lars Fagerstam, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 623 days.

(21) Appl. No.: 10/312,055

(22) PCT Filed: Jun. 29, 2001

(86) PCT No.: PCT/EP01/07474

§ 371 (c)(1),
(2), (4) Date: Jul. 11, 2003

(87) PCT Pub. No.: WO02/01217

PCT Pub. Date: Jan. 3, 2002

(65) Prior Publication Data

US 2004/0101974 A1    May 27, 2004

(30) Foreign Application Priority Data

Jun. 30, 2000   (GB)   ................... 0016010.1

(51) Int. Cl.
*B01L 3/00*        (2006.01)
*B01L 3/02*        (2006.01)
*B26D 7/06*        (2006.01)
*G01N 33/543*      (2006.01)
*C25B 11/00*       (2006.01)

(52) U.S. Cl. ..................... 422/99; 422/100; 83/24; 436/518; 204/606

(58) Field of Classification Search ................. 422/99, 422/100; 83/24; 436/518; 204/606
See application file for complete search history.

(56) References Cited

U.S. PATENT DOCUMENTS 4,354,406 A * 10/1982 Brun et al. .................... 83/24
4,684,613 A    8/1987 Barrere et al.
4,908,015 A *  3/1990 Anis .......................... 604/22
5,560,544 A * 10/1996 Merritt et al. .............. 239/104
5,587,062 A   12/1996 Togawa et al.
6,402,914 B1 * 6/2002 Goldsborough ............ 204/456

FOREIGN PATENT DOCUMENTS

WO    WO98/23950      6/1998
WO    WO 98/41610  *  9/1998
WO    WO99/15875      4/1999

OTHER PUBLICATIONS

LBL Human Genome Center, Automated Colony Sorting, 1993, http://www.lbl.gov/Science-Articles/ResearchReview/Highlights/1993/genetics-sequencing.html, pp. 1-2.*

(Continued)

*Primary Examiner*—Jill Warden
*Assistant Examiner*—Lore Ramillano
(74) *Attorney, Agent, or Firm*—Dwayne L. Bentley

(57) ABSTRACT

The present invention relates to devices and methods for removing gels plugs (47) from a gel(3) bonded to a surface (5) wherein means are provided for rotating the gel plug before lifting it from said surface. The rotation of the gel plug is intended to break the bond between said gel plug and said gel surface.

14 Claims, 2 Drawing Sheets

OTHER PUBLICATIONS

Jones et al., Integration of image analysis and robotics into a fully automated colony picking and plate handling system, Apr. 24, 1992, Oxford University Press, v. 20, No. 17, pp. 4599-4606.*

Stanford Genome Technology Center, Plaque Picker, Feb. 9, 1999, http://www.sequence-stanford.edu/group/techdev/picker.html, pp. 1-2 and plaque picker image.*

* cited by examiner

SPOT PICKER DEVICE AND METHOD FOR PICKING GEL PLUGS

FIELD OF THE INVENTION

The present invention relates to devices and methods for picking up spots of gel from sheets of gel.

PRIOR ART

Many biochemical analytical methods produce results in the form of sheets of gel upon which the constituents of the analysed substances are grouped in spots. Further analysis of the constituents can be made by cutting out and picking up the cylindrical plugs of gel containing the substances of interest and transferring the plugs to other devices such as microtitre plates or test tubes for further analysis. The plugs are extracted from the sheet of gel by lowering a cylindrical hollow needle through any liquid covering the gel and the gel until it reaches the supporting base plate, applying a suction to the upper end of the needle in order to lift the plug off the base plate and into the needle where it is caught by a pieced bulkhead near the tip of the needle. The plug can then be transported by the picker head to a position above a well in a micro-titre plate or a test tube and then ejected out of the needle by pressurised liquid applied to the upper part of the needle.

A problem can occur if the sheet of gel is bonded to an underlying support, as the tensile strength of the bond holding the gel to the support is greater than the tensile strength of the gel in the plug. This means that when a gel plug is sucked up, the top of the plug breaks away from the base of the plug of gel, leaving a stump of gel attached to the support. This means that some of the constituents of the sample of interest can remain behind on the gel sheet and are not available for further analysis.

SUMMARY OF THE INVENTION

The present invention seeks to provide a device and a method for overcoming the problem of the prior art devices and methods. The present invention achieves this with a device having the features mentioned in the characterising part of claim 1 and by means of a method having the features mentioned in the characterising part of claim 7. Further advantages of the present invention are obtained by means of devices and methods having the features of the dependent claims.

Devices and methods having the features of claims 1 and 7 have the advantage that a gel plug can be easily detached from a support that it is bonded to.

Devices having the feature of claim 2 have the advantage that no electrical supply is needed to rotate the gel plug.

Devices having the feature of claim 3 have the advantage that a connection between holder and body can be made that is relatively free from play and which therefore ensures good positioning accuracy and repeatability.

Devices having the feature of claim 4 have the advantage that the needle may be rotated as it is being lowered through the gel in order to break up the gel plug if desired. It is also possible to reduce the force with which the needle is pressed onto the underlying surface and thereby reduce the risk of damaging this surface.

Devices having the feature of claim 5 have the advantage that a needle rotation which is less than 360° is sufficient to break the bond between the gel and underlying surface.

Devices having the feature of claim 6 and methods having the features of claim 8 have the advantage that a gel plug can be ejected from each cavity independently of the other cavity/cavities.

DETAILED DESCRIPTION OF EMBODIMENTS ILLUSTRATING THE INVENTION

Figure 1:
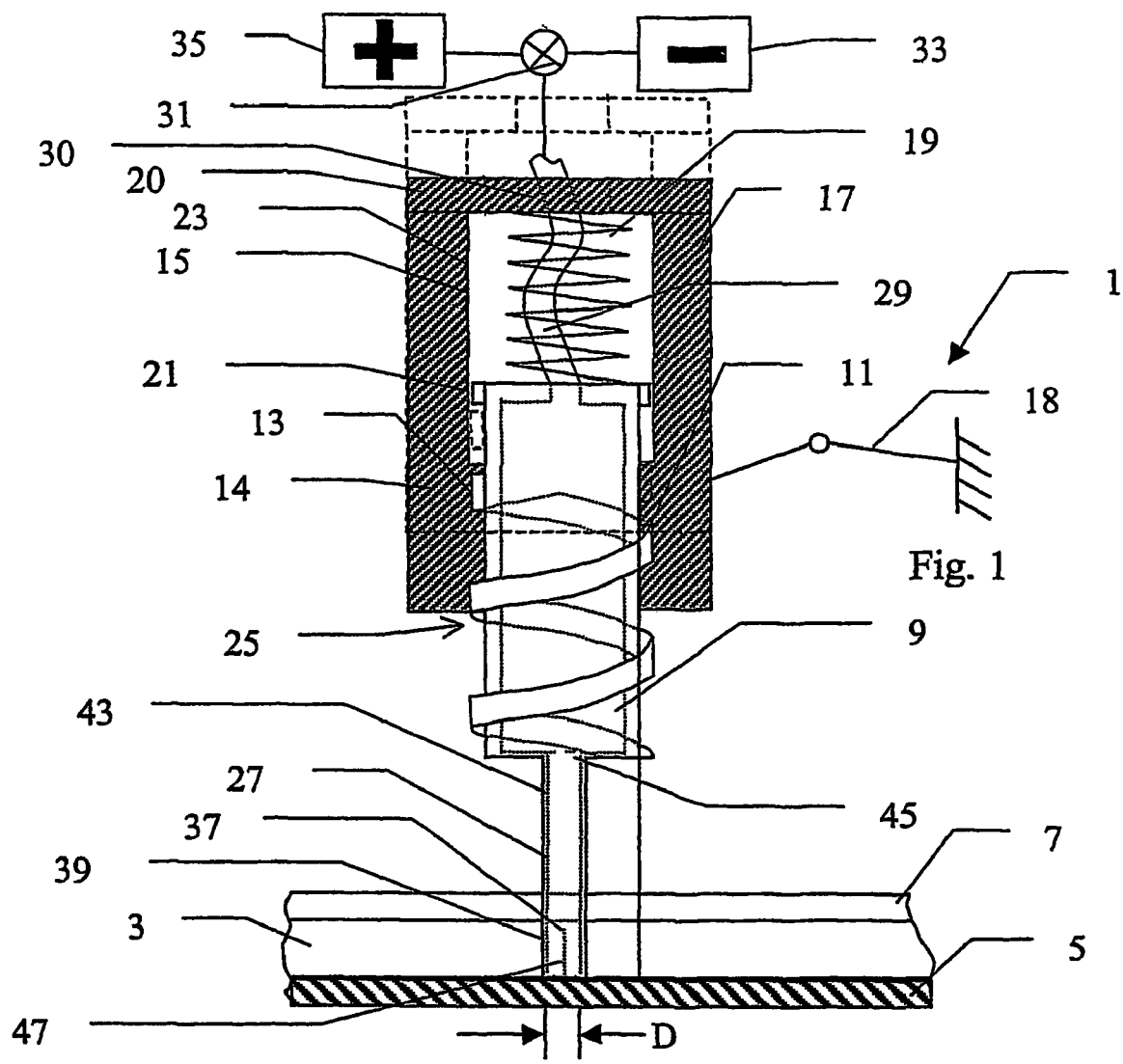
FIG. 1 shows a section along line I-I in FIG. 2 of a first embodiment of a spot picker head in accordance with the present invention.

FIG. 1 shows a lateral view of a picker head 1 for picking up plugs of gel from a sheet of gel 3. The sheet of gel 3 is bonded to a plate 5 and is covered by a thin layer of fluid 7 that prevents the gel from drying out. Picker head 1 has a tubular body 9 provided with an external thread 11. Body 9 is rotatably mounted in a complementing thread 13 in the lower portion 14 of the cylindrical inner wall 15 of a holder 17. Holder 17 is attachable to manoeuvring means such as a robot picker arm 18 (shown schematically). Holder 17 is provided with resilient means such as a helical spring 19 that acts against the lower surface of a, preferably removable, holder lid 20 to push body 9 towards the bottom of holder 17 (this position is shown by dashed lines in FIG. 1). Lid 20 limits the upward movement of body 9. Body 9 is provided with radially projecting means 21 which-are adapted to co-operate with the upper portion 23 of inner wall 15, which has a wider diameter than the threaded lower portion 14 of inner wall 15, in order to provide a means for limiting the downward movement of body 9 with respect to holder 17. The lower end of body 9 has an opening 25 to which a hollow needle 27 is attached. Needle 27 is open at each end and has an internal diameter D. The upper end of body 9 can be connected by means of a flexible pipe 29 to a valve 31. Flexible pipe 29 can preferably pass through a hole 30 in lid 20. Valve 31 is connectable to a supply of fluid 33 at a pressure lower than atmospheric pressure in order to form suction at the lower end of needle 27 in order to suck gels or other material of interest into needle 27. Valve 31 can also be connected to a supply of pressurised liquid 35 in order to form an overpressure at the lower end of needle 27 in order to blow out any gels or material of interest from needle 27. The pressurised liquid from supply 35 or a further supply of cleaning liquid (not shown) may also be subsequently used to clean the needle 27 to prevent cross-contamination of samples. Needle 27 contains a vertical bulkhead 37 that extends across the inside of bottom part 39 of needle 27 from the wall to the centre. The upper part 43 of needle 27 is provided with a perforated end bulkhead 45 which prevents material that is sucked into needle 27 from being sucked all the way up into the body 9.

Picker head 1 is shown in solid lines in FIG. 1 in a position where it has been lowered through the fluid 4 and the sheet of gel 3 and the bottom of needle 27 in contact with the plate 5. The needle 27 contains gel 47 that has been detached from the plate 5. The bonding between the gel and the plate 5 has been completely broken by rotation of bulkhead 37 through an angle of more than 360°. This can be achieved by the downward motion of the holder 17 being continued after the needle has been lowered through gel 3 into contact with the plate 5. This causes the thread on the inside of holder 17 to rotate body 9 up against the pressure of spring. This rotation causes the vertical bulkhead 37 also to rotate and therewith the plug of gel 47 inside needles 27. This rotation of gel 47 by the bottom of the bulkhead 37 adjusting valve 33 so that pipe 29 is connected to the fluid supply 33 that is at a pressure lower than atmospheric. Gel 47 is prevented from rising into the body 9 by perforated end bulkhead 45. The picker head 1 can be moved to a position above a collection vessel or surface and the gel 47 can then be rejected by adjusting valve 33 so that fluid from the pressurized fluid supply is connected to pipe 29.

Figure 2:
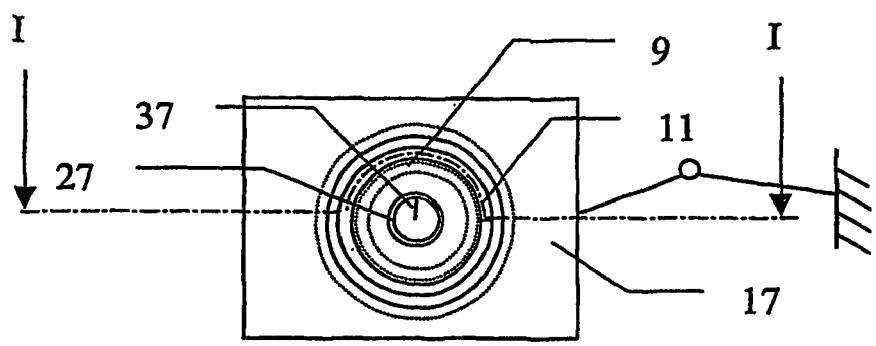
FIG. 2 shows a view from below of the spot picker head of FIG. 1.
Figure 3:
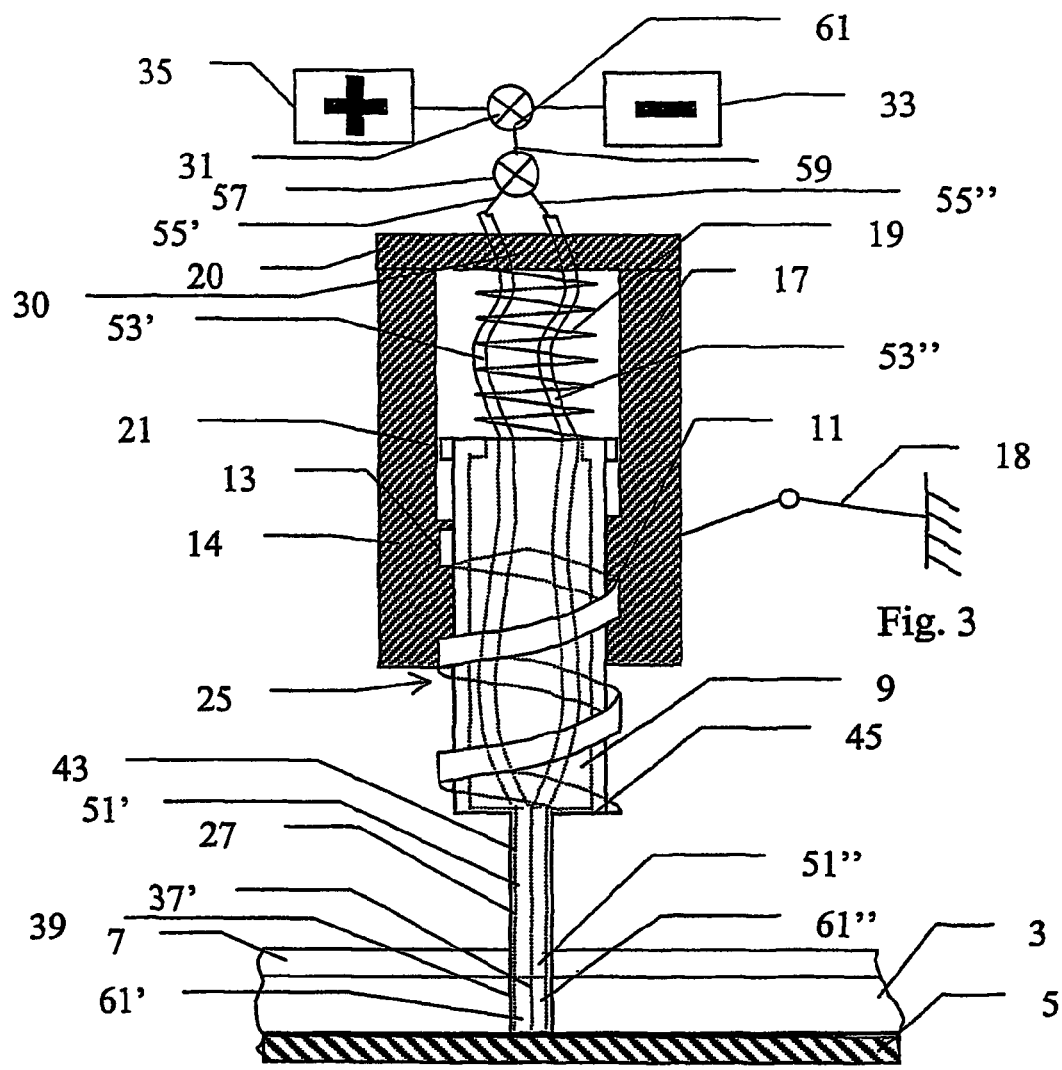
FIG. 3 shows a section along line I-I in FIG. 2 of a spot picker head in accordance with a second embodiment of the invention.
Figure 4:
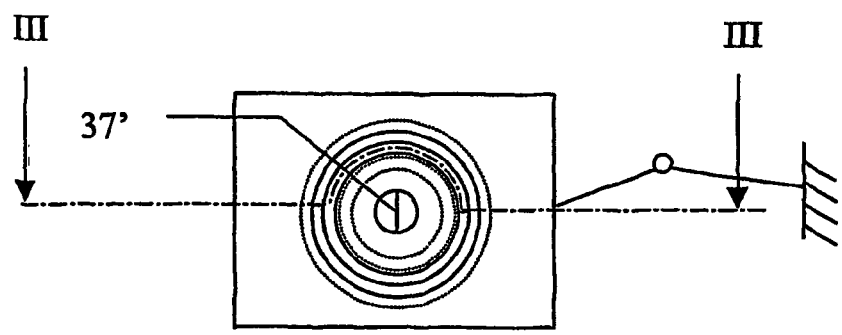
FIG. 4 shows a view from below of the spot picker head of FIG. 3.

FIGS. 3 and 4 show a second embodiment of a picker head in accordance with the present invention, wherein components having the same function as those in the first embodiment have the same reference numbers as used in FIGS. 1 and 2. In this embodiment needle 27 is provided with a vertical bulkhead 37' that extends across the width of needle 27 in order to form two substantially semi-cylindrical cavities 51', 51". Bulkhead 37' extends up to a perforated end bulkhead 45. Cavity 51' is connectable to a first flexible pipe 53' that extends up through the holder 17 to a first outlet 55' of a valve 57. Cavity 51" is connectable to a second flexible pipe 53" which extends up through the holder 17 to a second outlet 55" of a valve 57. Valve 57 has an inlet 59 that is connectable to the outlet 61 of a valve 31. Valve 31 has two inlets 63', 63" that can be selectively connected to two supplies of fluid, 33, 35, respectively, below and above atmospheric pressure. The valves 31, 57 are operable so that both pipes 53', 53" can be connected at the same time to the source of fluid below atmospheric pressure 33 in order to suck the semi-cylindrical gel plugs 61', 61" up into the needle 27. As described previously in connection with the first embodiment of the present invention, these semi-cylindrical plugs 61', 61" can be detached from the plate 3 by the downward motion of the holder 17 being continued after the needle had been lowered through gel 2 into contact with the plate 3. This causes the thread on the inside of holder 17 to rotate body 9 up against the pressure of spring 19. This rotation causes the vertical bulkhead 37' also to rotate and therewith the gel inside needle 27. If this rotation of the gel by the bottom of the bulkhead 37 is through an angle greater than 180° the gel can be scraped loose from the plate 3, thereby forming two semi-cylindrical plugs 61', 61". These plugs 61', 61" can be ejected from the needle 27 by connecting pipes 53', 53" separately, and preferably in turn, to the supply of fluid above atmospheric pressure 35 via valves 31, 57. In this way it can be assured that both plugs 61', 61" will be ejected. This is necessary, as if both pipes were connected simultaneously to the fluid supply via a single outlet then it is most likely that only one plug would be ejected e.g. plug 61'. This is because as soon as plug 61' was ejected the resistance to fluid flow through cavity 51' that is no longer was blocked by the plug 61' would be lower than that in cavity 51" that is still blocked by plug 61". As the pressurised fluid would take the path of least resistance through the needle it would not push the plug 61" out of the still blocked cavity 51" but would flow out of the unblocked cavity 51'. By connecting pipes 53', 53" separately to the fluid supply, the least possible fluid may be used and dilution of the items of interest from the gel by this fluid is minimised.

In the event that for reasons of manufacturing simplicity it is not desirable to use two pipes then it is possible to extract both gel plugs 61', 61" substantially simultaneously by using a single pipe. In this case, a high fluid flow rate would be needed and this would have the disadvantage that the plugs would be presented in a large volume of fluid which would have to be removed together with any salts dissolved in the fluid.

Figure 5A:
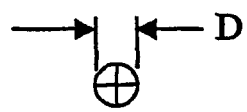
FIGS. 5*a*) and 5*b*) show views from below of two further embodiments of needles in accordance with the present invention.
Figure 5B:
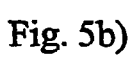

Other embodiments of the present invention are also conceivable. For example, the vertical bulkhead in the needle may be replaced by a plurality of angularly separated vertical bulkheads that would have the effect of reducing the angle that the needle has to rotate in order to detach the gel plug(s) from the underlying plate. Two examples of such pluralities of bulkheads are shown in FIGS. 5a) and 5b).

While the present invention has been illustrated by embodiments in which the rotation of the needle is caused by mechanical means is also conceivable to provide a spot picker with electric motor means for rotating the needle. This could be accomplished by providing the holder with an electric motor that can rotate the needle in the body or the body in the holder. The preferred embodiments use mechanical means as these avoid the use of electrical devices in the vicinity of fluids. However the use of an electric motor means that the needle can be rotated as it is being lowered through the gel. This can be used to break up the gel and can help release the chemicals of interest from the gel. Additionally, the downward movement of the needle can be stopped as soon as it touches the plate under the gel or even just before it touches the plate i.e. until it is adjacent the plate, and then the needle can be rotated without having to press onto the plate. This can shear of the gel plug just above its bond onto the plate. This reduces the scratching of the plate, which may otherwise occur, and thereby permits reuse of the plate at the expense of a small fraction of the gel plug being left on the plate.

The rotating movement of the needle does not have to be continuous in one direction but may be a reciprocating movement e.g. a rotation of say 90° in one direction followed by a rotation of 180° in the reverse direction. This would still enable the bond between the gel plug and plate to be broken while at the same time reducing the forces acting on the gel outside the needle.

It is further conceivable that the perforated bullhead that stops the upward movement of the gel is not positioned at the top of the needle. It may be positioned at an intermediate position that is at least at a distance from the bottom end of the needle which is greater or equal to the depth of the gel which is to be picked. This is advantageous because the closer the bulkhead is to bottom end of the needle than the less fluid is required to eject the plug(s) from the needle and therefore the dilution of the sample of interest is reduced.

The above mentioned embodiments are intended to illustrate the present invention and are not intended to limit the scope of protection claimed by the following claims.

What is claimed is:

1. A device for removing one or more gel plugs (47, 61', 61") from a sheet of gel (3) which is bonded to a plate (5) comprising:
   a needle (27) with an open end wherein the bottom part (39) of said needle (27) is provided with at least one internal bulkhead (37, 37') extending at least from a position on the inner wall of said needle (27) to the centre of said needle (27);

wherein said device has means (11, 13, 17) to rotate said needle (7), and thereby said at least one bulkhead, at a particular angle after it has been lowered into contact with, or adjacent to, said plate (5) said rotation of the needle (27) being performed until a bond between said at least one gel plug (47, 61', 61") and plate (5) is broken by the rotation of said at least one bulkhead; and the open end of the needle (27) is configured to extract at least one gel plug (47, 61', 61") from the plate (5) and receive the at least one gel plug (47, 61', 61") into the open end of the needle (27), and wherein the needle (27) is provided with another bulkhead (45) that is configured to prevent material associated with the at least one gel plug (47, 61', 61") that is sucked up into the needle (27) from being sucked up into a body (9) to which the needle (27) is attached.

2. The device of claim 1, wherein said means (11, 13, 17) for rotating said needle (27) include a threaded part (11) on an external surface of the body (9) to which said needle (27) is attachable, said body (9) is rotably mounted in a complementing thread (13) provided on an inner wall of a holder (17) in which said body (9) is provided.

3. The device of claim 1, wherein said means (11, 13, 17) for rotating said needle (27) comprise an electrical motor configured to rotate the needle (27) in the body (9) to which said needle (27) is attachable.

4. The device of claim 1, wherein at least one bulkhead (37') extends from a position on an inner wall of said needle (27) to another position on the inner wall of said needle (27) in order to form at least two cavities (51', 51").

5. The device of claim 1, wherein each cavity (51', 51") is connectable separately through separate pipes (53', 53") to a supply of pressurized fluid (35).

6. The device of claim 1, wherein the angle is greater than 180°.

7. The device of claim 1, wherein the angle is 90° in one direction and 180° in another direction.

8. The device of claim 1, wherein the another bulkhead (45) is a perforated end bulkhead (45).

9. A method for removing one or more gel plugs from a surface to which it is bonded comprising the steps of:

providing a needle (27) with at least one internal vertical bulkhead (37, 37') extending at least from a position on the inner wall of said needle (27) to the centre of said needle (27);

lowering said needle (27) through gel until it is in contact with said surface (3) to form at least one gel plug (47, 61', 61") inside said needle (27);

rotating said needle until the bond between said at least one gel plug (47, 61', 61") and surface (3) is broken by rotation of said at least one bulkhead;

sucking said at least one gel plug up into said needle (27) by connecting the needle to pressure lower than atmospheric; and providing the needle (27) with a another bulkhead (45) configured to prevent material associated with the at least one gel plug (47, 61', 61") that is sucked up into the needle (27) from being sucked up into a body (9) to which the needle (27) is attached.

10. The method of claim 9 further comprising:

providing a needle (27) with at least one internal bulkhead (37') that extends from a position on the inner wall of said needle (27) to another position on the wall of said needle (27) in order to form at least two cavities (51', 51"); and ejecting said at lest one gel plug (47, 61', 61") from said needle (27) by connecting each of said cavities separately to a supply of pressurised fluid (35).

11. A method for removing one or more gel plugs from a sheet of gel (3) which is bonded to a plate (5) comprising:

providing a needle (27) with at least one internal vertical bulkhead (37, 37') extending at least from a position on an inner wall of said needle (27) to the centre of said needle (27);

rotating said needle (27) at an angle while the lowering said needle (27) through said gel (3) until the needle (27) is in contact with, or adjacent to, said plate (5) to form at least one gel plug (47, 61 ',61") inside said needle (27);

rotating said needle (27) until a bond between said at least one gel plug (47, 61 '61") and plate (5) is broken by rotation of said at least one bulkhead; and providing the needle (27) with another bulkhead (45) configured to prevent material associated with the at least one gel plug (47, 61', 61") that is sucked up into the needle (27) from being sucked up into a body (9) to which the needle (27) is attached.

12. The method of claim 11, further comprising:

extracting said at least one gel plug (47, 61', 61") from the gel (3) into said needle (27).

13. The method of claim 12, further comprising:

connecting said needle (27) to a fluid supply (33), wherein the fluid supply (33) is configured to extract at least one gel plug (47, 61', 61") from the gel (3).

14. The method of claim 13, further comprising:

providing the needle (27) with the at least one internal bulkhead (37') that extends from a position on the inner wall of said needle (27) to another position on a wall of said needle (27) in order to form at least two cavities (51', 51"); and ejecting said at least one gel plug (47, 61',61") from the needle (27) by utilizing said needle (27) by connecting each of said cavities (51', 51") separately via pipes and valves to a supply of pressurized fluid (35).

\* \* \* \* \*